(12) United States Patent
Nishiyama et al.

(10) Patent No.: US 6,388,086 B1
(45) Date of Patent: May 14, 2002

(54) PROCESS FOR PRODUCTION OF 3-(3-PYRIDYL)-1-PROPANOL DERIVATIVES

(75) Inventors: Akira Nishiyama, Kakogawa; Kazumi Okuro, Kobe; Kenji Inoue, Kakogawa, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/631,678

(22) Filed: Aug. 2, 2000

(30) Foreign Application Priority Data

Aug. 2, 1999 (JP) ............................................. 11-218650
Aug. 10, 1999 (JP) ............................................. 11-226772

(51) Int. Cl.⁷ ............................................. C07D 213/30
(52) U.S. Cl. ..................................................... 546/344
(58) Field of Search ......................................... 546/344

(56) References Cited

U.S. PATENT DOCUMENTS 5,977,105 A * 11/1999 Cheshire et al. ............. 514/241

FOREIGN PATENT DOCUMENTS

| EP | 0 264 114 | 4/1988 |
| EP | 0 267 439 | 5/1988 |
| FR | 2 051 536 | 5/1970 |
| FR | 2 270 863 | 5/1975 |
| WO | WO 97/20815 | 6/1997 |
| WO | WO 98/43971 | 10/1998 |

OTHER PUBLICATIONS

Cram and Hammond, "Organic Chemistry", Mc–Graw Hill Book Co., NY, (1964) 2nd edition, pp. 565–567.*

* cited by examiner

Primary Examiner—Patricia L. Morris
(74) Attorney, Agent, or Firm—Connolly Bove Lodge & Hutz LLP

(57) ABSTRACT

A process for producing a 3-(3-pyridyl)-1-propanol derivative of use as a pharmaceutical intermediate expediently with an inexpensive material is provided. The process is concerned with a 3-(3-pyridyl)-1-propanol derivative (3):

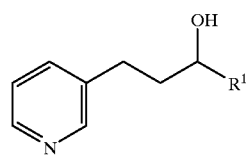

(3)

in the formula, $R^1$ represents an alkyl group of 1 to 20 carbon atoms, aryl group of 6 to 20 carbon atoms or aralkyl group of 7 to 20 carbon atoms, which may be substituted, and comprises reacting a 3-methylpyridine with a strong base to prepare a 3-methylpyridine metal (1):

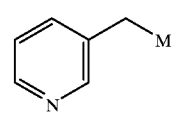

(1)

in the formula, M represents lithium, sodium, potassium or a magnesium halide, where the halide is chloride or bromide, and then reacting said metal salt with an epoxy compound (2):

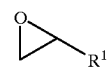

(2)

16 Claims, No Drawings

PROCESS FOR PRODUCTION OF 3-(3-PYRIDYL)-1-PROPANOL DERIVATIVES

TECHNICAL FIELD

The present invention is related to production of a pharmaceutical intermediate, particularly a 3-(3-pyridyl)-1-propanol derivative which is of value as an intermediate of tryptase inhibitors, especially a 4-(3-pyridyl)-1,2-butanediol.

PRIOR ART

Up to the present, the following processes are known for the production of 3-(3-pyridyl)-1-propanol derivatives.

(1) A process starting with 3-(3-pyridyl)-1-propionaldehyde
  which comprises subjecting the starting compound and trimethylsulfoxonium iodide to coupling reaction to synthesize 3-(2-oxiranylethyl)pyridine and reacting it with a phenol derivative or a thiol derivative (WO97/20815).
(2) A synthetic process starting with 3-(3-pyridyl)-1-propionaldehyde
  which comprises reacting this starting compound with an aryloxymethyllithium or arylthiomethyllithium prepared from an aryloxymethane or arylthiomethane and butyllithium (WO97/20815).
(3) A process
  which comprises reacting 3-(pyridyl)methyllithium prepared from 3-methylpyridine and the lithium base with epichlorohydrin to synthesize α-(chloromethyl)-3-pyridinepropanol, cyclizing it with a base to give an epoxide derivative and reacting this derivative with a phenol derivative or a thiol derivative (WO97/20815).
(4) A synthetic process starting with 3-pyridylmethyltriphenylphosphonium chloride hydrochloride
  which comprises subjecting this starting compound and 2,3-O-isopropylideneglyceraldehyde to coupling reaction and further subjecting the resulting 4-(3-pyridyl)-1,2-O-isoproylidenebut-3-ene-1,2-diol to olefin reduction and deacetonylation (WO98/42669).

However, the prior art processes (1) and (2) require expensive starting materials and, in addition, the product is invariably a racemic mixture which requires optical resolution. The prior art process (3) is not practically useful because the yield of the coupling reaction in the first step is low. The prior art process (4) uses very expensive starting materials. For these and other reasons, none of the prior art processes are efficient enough for commercial production.

SUMMARY OF THE INVENTION

In view of the above state of the art, the present invention has for its object to provide a process for producing a 3-(3-pyridyl)-1-propanol derivative of use as a pharmaceutical intermediate, particularly an 4-(3-pyridyl)-1,2-butanediol expediently with an inexpensive material.

The present invention, therefore, is directed to a process for producing a 3-(3-pyridyl)-1-propanol derivative (3):

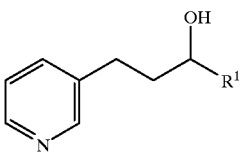

(3)

in the formula, $R^1$ represents an alkyl group of 1 to 20 carbon atoms, aryl group of 6 to 20 carbon atoms or aralkyl group of 7 to 20 carbon atoms, which may be substituted, which comprises reacting a 3-methylpyriding with a strong base to prepare a 3-methylpyridine metal (1):

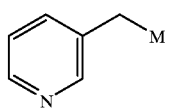

(1)

in the formula, M represents lithium, sodium, potassium or a magnesium halide, where the halide is chloride or bromide, and then reacting said metal salt with an epoxy compound (2):

(2)

in the formula, $R^1$ is as defined above, to give a 3-(3-pyridyl)-1-propanol derivative, wherein the 3-methylpyridine is used in molar in excess of said strong base, and/or the reaction between said metal salt and said epoxy compound is conducted in the presence of an amine.

The present invention is further directed to a process for producing a 4-(3-pyridyl)-1,2-butanediol (7):

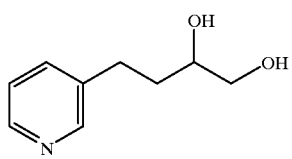

(7)

which comprises reacting a 3-methylpyridine with a strong base to prepare a 3-methylpyridine metal salt (1), then reacting said metal salt with an O-protected glycidol (5):

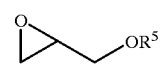

(5)

in the formula, $R^5$ represents a hydroxy-protecting group, to give a 1-O-protected-4-(3-pyridyl)-1,2-butanediol (6):

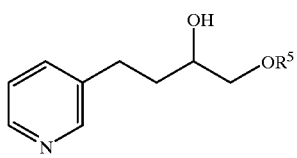

(6)

and deprotecting the same.

In addition, the present invention is directed to a process for producing an 1-O-protected-4-(3-pyridyl)-1,2-butanediol (6)
which comprises reacting 3-methylpyridine with a strong base to prepare a 3-methylpyridine metal salt (1)
and reacting said metal salt with an O-protected glycidol (5).

The present invention is now described in detail.

DETAILED DESCRIPTION OF THE INVENTION

Referring to the above general formula (1), M represents lithium, sodium, potassium or a magnesium halide, where the halide means chloride or bromide. Preferred is lithium.

Referring to the above general formulas (2) and (3), $R^1$ represents an alkyl group of 1 to 20 carbon atoms, aryl group of 6 to 20 carbon atoms or aralkyl group of 7 to 20 carbon atoms, which may be substituted. More particularly, $R^1$ includes but is not limited to methyl, ethyl, n-propyl, isopropyl, sec-butyl, tert-butyl, phenyl, benzyl, 2-phenylethyl, 2-(2-naphthyl)ethyl, 2-phenylvinyl, 2-(2-naphthyl)acetylene, chloromethyl, hydroxymethyl, p-toluenesulfonyloxymethyl, acetyloxymethyl, pivaloyloxymethyl, benzoyloxymethyl, phenyloxymethyl, 4-(phenyl)phenyloxymethyl, 4-[3'-(N,N-dimethylphenylacetamido)phenyl]phenyloxymethyl, 2-naphthyloxymethyl, 2-(6-bromonaphthyl)oxymethyl, 2-[6-(3-(N,N-dimethyl)propanamide)naphthyl]oxymethyl, benzyloxymethyl, tert-butyloxymethyl, aryloxymethyl, tert-butyldimethylsilyloxymethyl, 2-tetrahydropyranyloxymethyl, 1-(phenyloxy)ethyl, 1-(phenyloxy)-1-methylethyl, phenylthiomethyl, 2-naphthylthiomethyl, N,N-dibenzylamino, and N-phenyl-N-ethylaminomethyl.

In the epoxy compound represented by general formula (2), $R^1$ is preferably a group of the following general formula (4):

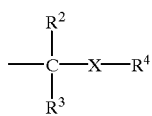

(4)

In the above general formula (4), $R^2$ and $R^3$ each independently represents hydrogen, an alkyl group of 1 to 18 carbon atoms, an aryl group of 6 to 18 carbon atoms or an aralkyl group of 7 to 18 carbon atoms, or $R^2$ and $R^3$, taken together, represent a cycloalkyl group of 3 to 18 carbon atoms. As specific groups, these include methyl, ethyl, n-propyl, isopropyl, sec-butyl, tert-butyl, phenyl, benzyl, cyclopropyl and cyclohexyl, among others. Particularly preferred is the case in which both $R^2$ and $R^3$ represent hydrogen.

$R^4$ represents hydrogen, an alkyl group of 1 to 18 carbon atoms, aryl group of 6 to 18 carbon atoms, aralkyl group of 7 to 18 carbon atoms or silyl group of 3 to 18 carbon atoms, which may be substituted. More particularly, $R^4$ includes methyl, ethyl, methoxyethyl, 2-trimethylsilylethyl, n-propyl, isopropyl, sec-butyl, tert-butyl, cyclopropyl, cyclohexyl, allyl, 2-tetrahydropyranyl, phenyl, p-nitrophenyl, o-chlorophenyl, 4-(phenyl)phenyl, 4-(3'-N,N-dimethylphenylacetamido)phenyl, 2-naphthyl, 2-(6-bromo) naphthyl, 2-(6-(3-N,N-dimethyl)propanamido)naphthyl, benzyl, p-nitrobenzyl, p-methoxybenzyl, phenethyl, trimethylsilyl, triethylsilyl, tert-butyldimethylsilyl and tert-butyldiphenylsilyl. Among these, $R^4$ is preferably phenyl, benzyl, tert-butyl or tert-butyldimethylsilyl.

X represents an oxygen atom or a sulfur atom. Preferred is an oxygen atom.

The process for producing a 3-(3-pyridyl)-1-propanol derivative in accordance with the present invention is now described.

Thus, the present invention is directed to a process for producing a 3-(3-pyridyl)-1-propanol derivative comprising permitting a strong base to act upon 3-methylpyridine to prepare a 3-methylpyridine metal salt and reacting said metal salt with an epoxy compound, wherein 3-methylpyridine is used in molar in excess of said strong base and/or the reaction between said metal salt and said epoxy compound is conducted in the presence of an amine.

Heretofore, this reaction involves many side reactions so that the yield is generally too low for commercial exploitation (e.g. WO97/20815). The present inventors discovered that the yield of the objective compound can be improved dramatically by reacting a molar excess of 3-methylpyridine with the strong base and/or conducting the reaction between said metal salt and epoxy compound in the presence of an amine. The present invention has been developed on the basis of the above finding.

The epoxy compound of the general formula (2) is not particularly restricted but includes, among others, propylene oxide, 1,2-epoxybutane, 1,2-epoxypentane, 1,2-epoxy-3-methylbutane, 1,2-epoxy-4-methylpentane, 1,2-epoxy-3,3-dimethylbutane, styrene oxide, 1,2-epoxy-4-phenylbutane, 1,2-epoxy-4-(2-naphthyl)butane, 1,2-epoxy-4-phenylbutene, 1,2-epoxy-4-(2-naphthyl)butyne, epichlorohydrin, glycidol, glycidyl tosylate, O-acetylglycidol, O-pivaloylglycidol, O-benzoylglycidol, phenyl glycidyl ether, 4-(phenyl)phenyl glycidyl ether, 4-[3'-(N,N-dimethylphenylacetamido)phenyl]phenyl glycidyl ether, 2-naphthyl glycidyl ether, 2-(6-bromonaphthyl) glycidylether, 2-[6-(3-(N,N-dimethyl)propanamido) naphthyl]glycidyl ether, benzyl glycidyl ether, tert-butyl glycidyl ether, allyl glycidyl ether, tert-butyldimethylsilyl glycidyl ether, 2-tetrahydropyranyl glycidyl ether, 1,2-epoxy-3-phenoxybutane, 1,2-epoxy-3-phenoxy-3-methylbutane, phenyl glycidyl thioether, 2-naphthyl glycidyl thioether, 2-(dibenzylamino)methyloxirane and 2-([ethyl(phenyl)amino]methyl)oxirane. Moreover, in the present invention, even when an optically active epoxy compound is used as a starting compound, the objective compound can be produced without being compromised in optical purity. Therefore, optically active forms of phenyl glycidyl ether, benzyl glycidyl ether, tert-butyl glycidyl ether, tert-butyl dimethylsilyl glycidyl ether, phenyl glycidyl thioether, etc. can be used with greater advantage.

The strong base mentioned above is not particularly restricted but includes alkyllithiums such as methyllithium, n-butyllithium, sec-butyllithium, tert-butyllithium, etc.;

Grignard reagents such as n-butylmagnesium chloride, n-butyl magnesium bromide, tert-butyl magnesium chloride, ethyl magnesium iodide, etc.; metal amides such as lithium amide, sodiumamide, potassiumamide, etc.; lithiumdialkylamides such as lithium diisopropylamide, lithium dicyclohexylamide, etc.; lithium disilylamides such as lithium hexamethyldisilazide, etc.; sodium dialkylamides such as sodium diisopropylamide etc.; potassium dialkylamides such as potassium diisopropylamide etc.; and halomagnesium dialkylamides obtainable from a Grignard reagent and a secondary amine, such as chloromagnesium diisopropylamide, bromomagnesium diisopropylamide, chloromagnesium dicyclohexylamide, and so on. The strong base preferably includes, among others, lithium dialkylamides such as lithium diisopropylamide, lithium dicyclohexylamide, etc., lithium disilylamides such as lithium hexamethyldisilazide etc., and halomagnesium dialkylamides such as chloromagnesium diisopropylamide, bromomagnesium diisopropylamide, chloromagnesium dicyclohexylamide, etc. Still more preferred are lithium dialkylamides such as lithium diisopropylamide, lithium dicyclohexylamide, etc. Particularly preferred is lithium diisopropylamide. These bases may be used each alone or in a suitable combination of 2 or more species. The amount of the strong base relative to the epoxy derivative is preferably 1 to 5 molar equivalents, more preferably 1 to 2 molar equivalents.

In this reaction, the yield of the objective compound can be dramatically improved by using 3-methylpyridine in a stoichiometrically excess amount relative to the strong base. Specifically, it is advantageous to use not less than 1.5 molar equivalents based on the strong base. Preferred range is 1.5 to 20 molar equivalents and more preferred range is 2 to 5 molar equivalents.

By conducting this reaction in the presence of an amine, the yield of the objective compound can be further improved. The amine which can be used for this purpose is not particularly restricted but includes ammonia; primary amines such as methylamine, cyclohexylamine, aniline, etc.; secondary amines such as dimethylamine, piperidine, morpholine, diisopropylamine, etc.; and tertiary amines such as N-methylmorpholine pyridine, N,N,N',N'-tetramethylethylenediamine, triethylamine, N,N-dimethylaniline, 1,8-diazabicyclo[5.4.0]undec-7-ene (DBU), and N,N-dimethylaminopyridine. In particular, tertiary amines such as N-methylmorpholine, pyridine, N,N,N',N'-tetramethylethylenediamine, triethylamine, N,N-dimethylaniline, 1,8-diazabicyclo[5.4.0]udec-7-ene (DBU), N,N-dimethylaminopyridine, etc. are more preferred from the viewpoint of improving product yields. Still more preferred is pyridine or triethylamine. These compounds can be used each alone or in a suitable combination of 2 or more species. The amount of the amine is preferably at least equimolar to the strong base, more preferably 1 to 20 molar equivalents, still more preferably 1 to 5 molar equivalents.

The reaction solvent to be used for this reaction is not particularly restricted but includes various ether series solvents such as diethyl ether, 1,2-dimethoxyethane, tert-butyl methyl ether, tetrahydrofuran, 1,4-dioxane, etc.; aliphatic hydrocarbon series solvents such as hexane, pentane, etc.; aromatic hydrocarbon series solvents such as benzene, toluene, xylene, etc.; urea series solvents such as N,N-dimethylpropyleneurea, N,N-dimethylethyleneurea, etc.; and phosphoric amide series solvents such as hexamethylphosphoric triamide and the like. Preferred are ether series solvents such as diethyl ether, 1,2-dimethoxyethane, tert-butyl methyl ether, tetrahydrofuran and 1,4-dioxane and more preferred is tetrahydrofuran. These solvents may be used each alone or in a suitable combination of 2 or more species.

The reaction temperature for this reaction is preferably not less than −20° C., more preferably −20° C. to 80° C., still more preferably −10° C. to 40° C.

The order of addition of reagents for this reaction may be arbitrary, although a typical sequence may comprise adding 3-methylpyridine to a solution of said strong base to carry out the first-step reaction for preferably 0.5 to 24 hours, more preferably 0.5 to 3 hours, and then adding said epoxy compound to carry out the second-step reaction for preferably 0.5 to 24 hours, more preferably 0.5 to 3 hours. The amine, when used, is preferably added prior to addition of the epoxy compound. More particularly, after addition of the amine, the reaction system is stirred for preferably 0.5 to 24 hours, more preferably 0.3 to 3 hours, and then the epoxy compound is added.

As the work-up procedure following this reaction, the standard method for recovery of a product from a reaction mixture can be utilized. For example, upon completion of said reaction, the reaction mixture is diluted with water and extracted with a standard extraction solvent, such as ethyl acetate, diethyl ether, methylene chloride, toluene, hexane, tetrahydrofuran or the like. Then, as the reaction solvent and extraction solvent are removed from the extract by distillation under heating and reduced pressure, the objective compound is obtained. The objective compound thus obtained can be further purified by the conventional purification procedure, such as crystallization for purification, fractional distillation, column chromatography and/or the like.

In the present invention, among 3-(3-pyridyl)-1-propanol derivatives (3), 1-O-protected-4-(3-pyridyl)-1,2-butanediols (6):

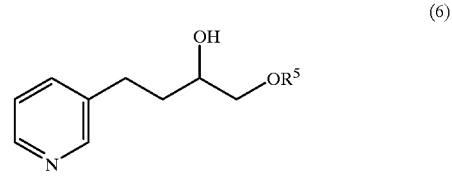

(6)

in particular, can be produced by reacting 3-methylpyridine with a strong base to prepare a 3-methylpyridine metal salt of said general formula (1) and reacting said metal salt with an O-protected glycidol (5):

(5)

in the formula, $R^5$ represents a hydroxy protecting group.

In addition, by deprotecting the 1-O-protected-4-(3-pyridyl)-1,2-butanediol thus obtained, there can be obtained 4-(3-pyridyl)-1,2-butanediol (7):

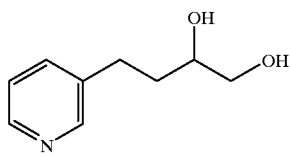

(7)

Referring to the above general formulas (5) and (6), $R^5$ represents a hydroxy-protective group, which is not particularly restricted but may be any conventional protective group for hydroxyl function. Thus, it includes the protective groups mentioned in Theodora W. Greene, Protective Groups in Organic Synthesis, 2nd Ed., John Wiley & Sons [1990] on pages 14 to 118, namely ether-type protective groups such as methoxymethyl, tert-butyl, tetrahydropyranyl, tetrahydrofuranyl, 2-(trimethylsilyl) ethoxymethyl, 1-methyl-1-methoxyethyl, 1-methyl-1-benzyloxyethyl, 2-(trimethylsilyl)ethyl, allyl, benzyl, p-methoxybenzyl, p-nitrobenzyl, diphenylmethyl, phenethyl, triphenylmethyl, etc.; silyl-type protective groups such as trimethylsilyl, triethylsilyl, tert-butyldimethylsilyl, tert-butyldiphenylsilyl, etc.; acetyl, benzoyl, pivaloyl, methyloxycarbonyl, ethyloxycarbonyl, benzyloxycarbonyl, tert-butyloxycarbonyl, etc. Preferred are ether-type protective groups and silyl-type protective groups, and more preferred are benzyl series protective groups, which may have a substituted group, such as benzyl, p-methoxybenzyl, p-nitrobenzyl and so on. Still more preferred protective group is benzyl.

The process for producing an 1-O-protected-4-(3-pyridyl)-1,2-butanediol according to the present invention is now described.

Thus, 3-methylpyridine is reacted with a strong base to prepare a 3-methylpyridine metal salt (1) which is then reacted with an O-protected glycidol (5) to synthesize an 1-O-protected-4-(3-pyridyl)-1,2-butanediol (6).

The O-protected glycidol (5) includes benzyl glycidyl ether, tert-butyl glycidyl ether, tetrahydropyranyl glycidyl ether, trimethylsilyl glycidyl ether, tert-butyldimethylsilyl glycidyl ether and O-tert-butyloxycarbonylglycidol. Preferred is benzyl glycidyl ether. Furthermore, in the present invention, even when an optically active O-protected glycidol is used as a starting compound, the objective compound can be produced without being compromised in optical purity. Therefore, it is more preferred to use an optically active benzyl glycidyl ether.

The strong base mentioned above is not particularly restricted but includes the same bases as mentioned hereinbefore. Preferred are lithium dialkylamides such as lithium diisopropylamide, lithium dicyclohexylamide, etc.; lithium disilylamides such as lithium hexamethyldisilazide etc.; and halomagnesium dialkylamides such as chloromagnesium diisopropylamide, bromomagnesium diisopropylamide, chloromagnesium dicyclohexylamide, and so on. More preferred are lithium dialkylamides such as lithium diisopropylamide, lithium dicyclohexylamide, etc., and still more preferred is lithium diisopropylamide. These bases can be used each alone or in a suitable combination of 2 or more species. The amount of use of the strong base is 1 to 5 molar equivalents, preferably 1 to 2 molar equivalents, based on the O-protected glycidol (5).

The amount of use of 3-methylpyridine based on the strong base is 1 to 10 molar equivalents. Particularly when 3-methylpyridine is used in a proportion of not less than 1.5 molar equivalents, the production yield of the 1-O-protected 4-(3-pyridyl)-1,2-butanediol is dramatically improved. Therefore, preferred ratio to the strong base is 1.5 to 5 molar equivalents.

By conducting this reaction in the presence of an amine, the yield of the objective compound can be further improved. The amine is not particularly restricted but includes the same species as mentioned hereinbefore. In particular, tertiary amines such as N-methylmorpholine, pyridine, N,N,N',N'-tetramethylethylenediamine, triethylamine, N,N-dimethylaniline, 1,8-diazabicyclo[5.4.0]undec-7-ene (DBU), N,N-dimethylaminopyridine, etc. are preferred from the viewpoint of improving yield. Still more preferred is pyridine or triethylamine. These amines can be used each alone or in a suitable combination of 2 or more species. The amount of use of the amine is preferably 1 to 20 molar equivalents, more preferably 1 to 5 molar equivalents, based on the strong base.

The reaction solvent for this reaction is not particularly restricted but includes the same solvents as mentioned hereinbefore. Preferred are ether series solvents such as diethyl ether, 1,2-dimethoxyethane, tert-butyl methyl ether, tetrahydrofuran, 1,4-dioxane, etc. More preferred is tetrahydrofuran. These solvents can be used each alone or as a suitable mixture of 2 or more species.

The reaction temperature for this reaction is preferably not less than −20° C., more preferably −20° C. to 80° C., still more preferably −10° C. to 40° C.

The order of addition of reagents for this reaction may be arbitrary, although a typical sequence may comprise adding 3-methylpyridine to a solution of said strong base to carry out the first-step reaction for preferably 0.5 to 24 hours, more preferably 0.5 to 3 hours, and then adding said O-protected glycidol (5) to carry out the second-step reaction for preferably 0.5 to 24 hours, more preferably 0.5 to 3 hours. The amine, when used, is preferably added prior to addition of the O-protected glycidol. More particularly, after addition of the amine, the reaction mixture is stirred for preferably 0.5 to 24 hours, more preferably 0.3 to 3 hours, and then the O-protected glycidol is added.

As the work-up procedure following this reaction, the standard procedure for recovery of a product from a reaction mixture can be utilized. For example, upon completion of said reaction, the reaction mixture is diluted with water and extracted with the common extraction solvent, such as ethyl acetate, diethyl ether, methylene chloride, toluene, hexane, tetrahydrofuran or the like. Then, as the reaction solvent and extraction solvent are removed from the extract by distillation under heating and reduced pressure, the objective compound is obtained. The objective compound thus obtained can be further purified by the conventional purification procedure such as crystallization for purification, fractional distillation, column chromatography and the like.

It should be noted that the 1-O-benzyl-4-(3-pyridyl)-1,2-butanediol and (2R)-1-O-benzyl-4-(3-pyridyl)-1,2-butanediol (8):

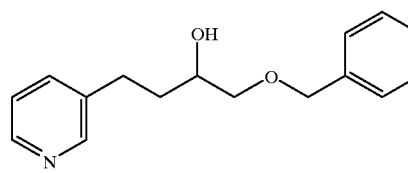

(8)

which can be obtained by this reaction are novel compounds not heretofore described in the literature.

The process for producing a 4-(3-pyridyl)-1,2-butanediol (7) is now described.

Thus, an 1-O-protected-4-(3-pyridyl)-1,2-butanediol is deprotected to give a 4-(3-pyridyl)-1,2-butanediol.

The deprotection procedure can be selected according to the species of protective group used from among the conventional procedures described in Theodora W. Greene, Protective Groups in Organic Synthesis, 2nd Ed., John Wiley & Sons, 1990 on pages 14 to 118.

By way of illustration, when $R^5$ in the compound (6) is a benzyl group, the compound can be deprotected using hydrogen in the presence of a palladium catalyst.

The present invention, constituted as above, enables production of pharmaceutical intermediates, particularly 3-(3-pyridyl)-1-propanol derivatives which are of value as intermediates of tryptase inhibitors, especially 4-(3-pyridyl)-1,2-butanediol, from inexpensive and readily available starting compounds.

EXAMPLES

The following examples are intended to illustrate the present invention in further detail and should by no means be construed as defining the scope of the invention.

Example 1

Production of 1-O-benzyl-4-(3-pyridyl)-1,2-butanediol

Under argon gas, a solution of diisopropylamine (3.34 g, 33 mmol) in tetrahydrofuran (5 mL) was added dropwise to n-butyllithium (1.53 M in hexane, 19.6 mL, 30 mmol) at 5° C. and the mixture was stirred for 30 minutes. To this was added a solution of 3-methylpyridine (4.191 g, 45 mmol) in tetrahydrofuran (5 mL) dropwise at 5° C., and the mixture was stirred for 30 minutes. Then, a solution of benzyl glycidyl ether (3.284 g, 20 mmol) in tetrahydrofuran (5 mL) was added at 5° C. and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give 7.189 g of a yellow oil. This oil was analyzed quantitatively by high-performance liquid chromatography [column: Nacalai-Tesque's Cosmosil 5CN-R (4.6 mm×250 mm), eluent: acetonitrile/phosphate buffer (pH 2.4)=1/100, flow rate: 0.5 mL/min., detection: UV210 nm, column temperature: 40° C.]. The production yield, thus found, of 1-O-benzyl-4-(3-pyridyl)-1,2-butanediol was 73%.

Example 2

Production of 1-O-benzyl-4-(3-pyridyl)-1,2-butanediol

Under argon gas, a solution of diisopropylamine (3.34 g, 33 mmol) in tetrahydrofuran (5 mL) was added dropwise to n-butyllithium (1.53 M in hexane, 19.6 mL, 30 mmol) at 5° C. and the mixture was stirred for 30 minutes. To this was further added a solution of 3-methylpyridine (5.588 g, 60 mmol) in tetrahydrofuran (5 mL) dropwise at 5° C., and the mixture was stirred for 30 minutes. Then, a solution of benzyl glycidyl ether (3.284 g, 20 mmol) in tetrahydrofuran (5 mL) was added at 5° C. and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give 8.587 g of a yellow oil. This oil was analyzed quantitatively by high-performance liquid chromatography [column: Nacalai-Tesque's Cosmosil 5CN-R (4.6 mm×250 mm), eluent: acetonitrile/phosphate buffer (pH 2.4)=1/100, flow rate: 0.5 mL/min., detection: UV210 nm, column temperature: 40° C.]. The production yield, thus found, of 1-O-benzyl-4-(3-pyridyl)-1,2-butanediol was 93%.

Example 3

Production of (2R)-1-O-benzyl-4-(3-pyridyl)-1,2-butanediol

Under argon gas, a solution of diisopropylamine (25.04 g, 247.5 mmol) in tetrahydrofuran (30 mL) was added dropwise to n-butyllithium (1.53 M in hexane, 147 mL, 225 mmol) at 10° C. and the mixture was stirred for 30 minutes. To this was further added a solution of 3-methylpyridine (41.85 g, 300 mmol) in tetrahydrofuran (30 mL) dropwise at 5° C., and the mixture was stirred for 30 minutes. Then, a solution of (R)-benzyl glycidyl ether (25.11 g, 150 mmol, 98.8% ee) in tetrahydrofuran (30 mL) was added dropwise over 30 minutes at 10° C. and the reaction was carried out at 5° C. for 1.5 hours. This reaction mixture was diluted with 225 mL of water for hydrolysis, and extracted with 225 mL of ethyl acetate. The organic layer was washed with 100 mL of water twice and the solvent was distilled off under reduced pressure to give 74.00 g of a yellow oil. This oil was purified by silica gel column chromatography (Merck's Kieselgel 60, hexane/ethyl acetate=1/2) to give 35.15 g (purity: 91.1 wt. %, isolation yield: 83%) of (2R)-1-O-benzyl-4-(3-pyridyl)-1,2-butandiol (yellow oil).

Example 4

Production of 1-O-tert-butyl-4-(3-pyridyl)-1,2-butanediol

Under argon gas, a solution of diisopropylamine (3.34 g, 33 mmol) in tetrahydrofuran (5 mL) was added dropwise to n-butyllithium (1.53 M in hexane, 19.6 mL, 30 mmol) at 5° C. and the mixture was stirred for 30 minutes. To this was further added a solution of 3-methylpyridine (5.588 g, 60 mmol) in tetrahydrofuran (5 mL) dropwise at 5° C., and the mixture was stirred for 30 minutes. Then, a solution of tert-butyl glycidyl ether (2.60 g, 20 mmol) in tetrahydrofuran (5 mL) was added at 5° C., and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give 9.375 g of a deep-red oil. This oil was purified by silica gel column chromatography (Merck's Kieselgel 60, hexane/ethyl acetate=1/2) to give 3.473 g (isolation yield: 78%) of 1-O-tert-butyl-4-( 3-pyridyl)-1,2-butanediol (yellow oil).

$^1$H-NMR (400 MHz, CDCl$_3$) δ: 1.19 (s, 9H), 1.69–1.81 (m, 2H), 2.58 (bs, 1H), 2.67–2.75 (m, 1H), 2.81–2.88 (m, 1H), 3.20 (dd, 1H), 3.37 (dd, 1H), 3.67–3.71 (bs, 1H), 7.20–7.27 (m, 1H), 7.52–7.55 (m, 1H), 8.43–8.48 (m, 2H).

Example 5

Production of 1-O-(tert-butyldimethylsilyl)-4-(3-pyridyl)-1,2-butanediol

Under argon gas, a solution of diisopropylamine (2.51 g, 24.75 mmol) in tetrahydrofuran (5 mL) was added dropwise to n-butyllithium (1.53 M in hexane, 14.71 mL, 22.5 mmol)

at 5° C. and the mixture was stirred for 30 minutes. To this was further added a solution of 3-methylpyridine (4.19 g, 45 mmol) in tetrahydrofuran (5 mL) dropwise at 5° C., and the mixture was stirred for 30 minutes. Then, a solution of tert-butyldimethylsilyl glycidyl ether (2.82 g, 15 mmol) in tetrahydrofuran (5 mL) was added at 5° C. and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give 6.164 g of a deep-red oil. This oil was purified by silica gel column chromatography (Merck's Kieselgel 60, hexane/ethyl acetate=1/2) to give 2.39 g (isolation yield: 66%) of 1-O-(tert-butyldimethylsilyl)-4-(3-pyridyl)-1,2-butanediol (yellow oil).

$^1$H-NMR (400 MHz, CDCl$_3$) δ: 0.07 (s, 6H), 0.90 (s, 9H), 1.65–1.98 (m, 2H), 2.63–2.74 (m, 3H), 3.36–3.57 (m, 3H), 7.19–7.22 (m, 1H), 7.50–7.55 (m, 1H), 8.43–8.44 (m, 2H).

Example 6

Production of 1-O-phenyl-4-(3-pyridyl)-1,2-butanediol

Under argon gas, a solution of diisopropylamine (1.67 g, 16.5 mmol) in tetrahydrofuran (5 mL) was added dropwise to n-butyllithium (1.53 M in hexane, 9.8 mL, 15 mmol) at 5° C. and the mixture was stirred for 30 minutes. To this was further added a solution of 3-methylpyridine (2.794 g, 30 mmol) in tetrahydrofuran (5 mL) dropwise at 5° C., and the mixture was stirred for 30 minutes. Then, a solution of phenyl glycidyl ether (1.50 g, 10 mmol) in tetrahydrofuran (5 mL) was added at 5° C. and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give a deep-red oil. This oil was purified by silica gel column chromatography (Merck's Kieselgel 60, hexane/ethyl acetate=1/2) to give 1.911 g (isolation yield: 79%) of 1-O-phenyl-4-(3-pyridyl)-1,2-butanediol (yellow oil).

$^1$H-NMR (400 HMz, CDCl$_3$) δ: 1.83–1.96 (m, 2H), 2.74–2.82 (m, 1H), 2.87–2.95 (m, 1H), 3.86–3.90 (m, 1H), 3.95–4.03 (m, 2H), 6.88–6.98 (m, 3H), 7.21–7.30 (m, 3H), 7.56 (d, 1H), 8.44–8.50 (m, 2H).

Example 7

Production of 1-(phenylsulfanyl)-4-pyridin-3-ylbutan-2-ol

Under argon gas, a solution of diisopropylamine (0.835 g, 8.25 mmol) in tetrahydrofuran (5 mL) was added dropwise to n-butyllithium (1.53 M in hexane, 4.9 mL, 7.5 mmol) at 5° C. and the mixture was stirred for 30 minutes. To this was further added a solution of 3-methylpyridine (1.40 g, 15 mmol) in tetrahydrofuran (5 mL) dropwise at 5° C., and the mixture was stirred for 30 minutes. Then, a solution of phenyl glycidyl thioether (0.83 g, 5 mmol) in tetrahydrofuran (5 mL) was added at 5° C. and the reaction was carried out for 2 hours. This reaction mixture was diluted with 10 mL of water for hydrolysis, and extracted with 20 mL of ethyl acetate. The organic layer was washed with 10 mL of water twice and the solvent was distilled off under reduced pressure to give a deep-red oil. This oil was purified by silica gel column chromatography (Merck's Kieselgel 60, hexane/ethyl acetate=1/2) to give 0.521 g (isolation yield: 41%) of 1-(phenylsulfanyl)-4-pyridin-3-ylbutan-2-ol (yellow oil).

$^1$H-NMR (400 MHz, CDCl$_3$) δ: 1.81–1.86 (m, 2H), 2.65–2.72 (m, 1H), 2.79–2.93 (m, 3H), 3.13 (dd, 1H), 3.65–3.71 (m, 1H), 7.18–7.38 (m, 6H), 7.49 (d, 1H), 8.41–8.43 (m, 2H).

Example 8

Production of 1-pyridin-3-ylpentan-3-ol

Under argon gas, a solution of diisopropylamine (3.34 g, 33 mmol) in tetrahydrofuran (5 mL) was added dropwise to n-butyllithium (1.53 M in hexane, 18.2 mL, 30 mmol) at 5° C. and the mixture was stirred for 30 minutes. To this was further added a solution of 3-methylpyridine (5.588 g, 60 mmol) in tetrahydrofuran (5 mL) dropwise at 5° C., and the mixture was stirred for 30 minutes. Then, a solution of 1,2-epoxybutane (1.420 g, 20 mmol) in tetrahydrofuran (5 mL) was added at 5° C. and the reaction was carried out for 2 hours. This reaction mixture was diluted with 30 mL of water for hydrolysis, and extracted with 30 mL of ethyl acetate. The organic layer was washed with 30 mL of water twice and the solvent was distilled off under reduced pressure to give 5.538 g of a yellow oil. This oil was purified by silica gel column chromatography (Merck's Kieselgel 60, hexane/ethyl acetate=1/1) to give 1.840 g (isolation yield: 53%) of 1-pyridin-3-ylpentan-3-ol (light-yellow oil).

$^1$H-NMR (400 MHz, CDCl$_3$) δ: 0.95 (t, 3H), 1.42–1.58 (m, 2H), 1.68–1.86 (m, 2H), 2.19–2.30 (bs, 1H), 2.62–2.73 (m, 1H), 2.77–2.90 (m, 1H), 3.52–3.59 (m, 1H), 7.18–7.26 (m, 1H), 7.52 (d, 1H), 8.39–8.50 (m, 2H).

Example 9

Production of 1-[ethyl(phenyl)amino]-4-pyridin-3-ylbutan-2-ol

Under argon gas, a solution of diisopropylamine (1.67 g, 16.5 mmol) in tetrahydrofuran (5 mL) was added dropwise to n-butyllithium (1.53 M in hexane, 9.8 mL, 15 mmol) at 5° C. and the mixture was stirred for 30 minutes. To this was further added a solution of 3-methylpyridine (2.794 g, 30 mmol) in tetrahydrofuran (5 mL) dropwise at 5° C. and the mixture was stirred for 30 minutes. Then, a solution of 2-([ethyl(phenyl)amino]methyl)oxirane (1.77 g, 10 mmol) in tetrahydrofuran (5 mL) was added at 5° C., and the reaction was carried out for 2 hours. This reaction mixture was diluted with 20 mL of water for hydrolysis, and extracted with 20 mL of ethyl acetate. The organic layer was washed with 20 mL of water twice and the solvent was distilled off under reduced pressure to give a yellow oil. This oil was purified by silica gel column chromatography (Merck's Kieselgel 60, hexane/ethyl acetate=1/1) to give 2.322 g (isolation yield: 86%) of 1-[ethyl(phenyl)amino]-4-pyridin-3-ylbutan-2-ol (yellow oil).

$^1$H-NMR (400 MHz, CDCl$_3$) δ: 1.12 (t, 3H), 1.77–1.83 (m, 2H), 2.70–2.77 (m, 1H), 2.88–2.95 (m, 1H), 3.13–3.19 (m, 1H), 3.29–3.48 (m, 3H), 3.88–3.93 (m, 1H), 6.73–6.79 (m, 3H), 7.20–7.26 (m, 3H), 7.54 (d, 1H), 8.43–8.49 (m, 2H).

Example 10

Production of 1-O-benzyl-4-(3-pyridyl)-1,2-butanediol

Under argon gas, a solution of diisopropylamine (3.34 g, 33 mmol) in tetrahydrofuran (5 mL) was added dropwise to n-butyllithium (1.53 M in hexane, 19.6 mL, 30 mmol) at 5° C. and the mixture was stirred for 30 minutes. To this was further added a solution of 3-methylpyridine (2.794 g, 30 mmol) in tetrahydrofuran (5 mL) dropwise at 5° C., and the mixture was stirred for 30 minutes. Then, pyridine (2.370 g, 30 mmol) was added and the mixture was further stirred at 5° C. for 30 minutes. To this was added a solution of benzyl glycidyl ether (3.284 g, 20 mmol) in tetrahydrofuran (5 mL) at 5° C., and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give 8.100 g of a yellow oil. This oil was analyzed quantitatively by high-performance liquid chromatography [column: Nacalai-Tesque's Cosmosil 5CN-R (4.6 mm×250 mm), eluent: acetonitrile/phosphate buffer (pH 2.4)=1/100, flow rate: 0.5 mL/min., detection: UV210 nm, column temperature: 40° C.]. The production yield, thus found, of 1-O-benzyl-4-(3-pyridyl)-1,2-butanediol was 59%.

Example 11

Production of 1-O-benzyl-4-(3-pyridyl)-1,2-butanediol

Under argon gas, a solution of diisopropylamine (3.34 g, 33 mmol) in tetrahydrofuran (5 mL) was added dropwise to n-butyllithium (1.53 M in hexane, 19.6 mL, 30 mmol) at 5° C. and the mixture was stirred for 30 minutes. To this was further added a solution of 3-methylpyridine (2.794 g, 30 mmol) in tetrahydrofuran (5 mL) dropwise at 5° C., and the mixture was stirred for 30 minutes. Then, N,N,N',N'-tetramethylethylenediamine (2.794 g, 30 mmol) was added and the mixture was further stirred at 5° C. for 30 minutes. To this was added a solution of benzyl glycidyl ether (3.284 g, 20 mmol) in tetrahydrofuran (5 mL) at 5° C., and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give 7.512 g of a yellow oil. This oil was analyzed quantitatively by high-performance liquid chromatography [column: Nacalai-Tesque's Cosmosil 5CN-R (4.6 mm×250 mm), eluent: acetonitrile/phosphate buffer (pH 2.4)=1/100, flow rate: 0.5 mL/min., detection: UV210 nm, column temperature: 40° C.]. The production yield, thus found, of 1-O-benzyl-4-(3-pyridyl)-1,2-butanediol was 42%.

Example 12

Production of 1-O-benzyl-4-(3-pyridyl)-1,2-butanediol

Under argon gas, a solution of diisopropylamine (3.34 g, 33 mmol) in tetrahydrofuran (5 mL) was added dropwise to n-butyllithium (1.53 M in hexane, 19.6 mL, 30 mmol) at 5° C. and the mixture was stirred for 30 minutes. To this was further added a solution of 3-methylpyridine (2.794 g, 30 mmol) in tetrahydrofuran (5 mL) dropwise at 5° C., and the mixture was stirred for 30 minutes. Then, triethylamine (3.040 g, 30 mmol) was added and the mixture was further stirred at 5° C. for 30 minutes. To this was added a solution of benzyl glycidyl ether (3.284 g, 20 mmol) in tetrahydrofuran (5 mL) at 5° C., and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give 7.266 g of a yellow oil. This oil was analyzed quantitatively by high-performance liquid chromatography [column: Nacalai-Tesque's Cosmosil 5CN-R (4.6 mm×250 mm), eluent: acetonitrile/phosphate buffer (pH 2.4)=1/100, flow rate: 0.5 mL/min., detection: UV210 nm, column temperature: 40° C.]. The production yield, thus found, of 1-O-benzyl-4-(3-pyridyl)-1,2-butanediol was 55%.

Example 13

Production of 1-O-benzyl-4-(3-pyridyl)-1,2-butanediol

Under argon gas, a solution of diisopropylamine (3.34 g, 33 mmol) in tetrahydrofuran (5 mL) was added dropwise to n-butyllithium (1.53 M in hexane, 19.6 mL, 30 mmol) at 5° C. and the mixture was stirred for 30 minutes. To this was added a solution of 3-methylpyridine (2.794 g, 30 mmol) in tetrahydrofuran (5 mL) dropwise at 5° C., and the mixture was stirred for 30 minutes. Then, 1,8-diazabicyclo[5.4.0]undec-7-ene (DBU) (4.56 g, 30 mmol) was added and the mixture was further stirred at 5° C. for 30 minutes. To this was added a solution of benzyl glycidyl ether (3.284 g, 20 mmol) in tetrahydrofuran (5 mL) at 5° C., and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give 7.266 g of a yellow oil. This oil was analyzed quantitatively by high-performance liquid chromatography [column: Nacalai-Tesque's Cosmosil 5CN-R (4.6 mm×250 mm), eluent: acetonitrile/phosphate buffer (pH 2.4)=1/100, flow rate: 0.5 mL/min., detection: UV210 nm, column temperature: 40° C.]. The production yield, thus found, of 1-O-benzyl-4-(3-pyridyl)-1,2-butanediol was 52%.

Example 14

Production of 1-O-benzyl-4-(3-pyridyl)-1,2-butanediol

Under argon gas, a solution of diisopropylamine (3.34 g, 33 mmol) in tetrahydrofuran (5 mL) was added dropwise to n-butyllithium (1.53 M in hexane, 19.6 mL, 30 mmol) at 5° C. and the mixture was stirred for 30 minutes. To this was further added a solution of 3-methylpyridine (2.794 g, 30 mmol) in tetrahydrofuran (5 mL) dropwise at 5° C., and the mixture was stirred for 30 minutes. Then, N,N-dimethylaniline (3.64 g, 30 mmol) was added and the mixture was further stirred at 5° C. for 30 minutes. To this was added a solution of benzyl glycidyl ether (3.284 g, 20 mmol) in tetrahydrofuran (5 mL) at 5° C., and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give 7.266 g of a yellow oil. This oil was analyzed quantitatively by high-performance liquid chromatography [column: Nacalai-Tesque's Cosmosil 5CN-R (4.6 mm×250 mm), eluent: acetonitrile/phosphate buffer (pH 2.4)=1/100, flow rate: 0.5 mL/min., detection: UV210 nm, column temperature: 40° C.]. The production yield, thus found, of 1-O-benzyl-4-(3-pyridyl)-1,2-butanediol was 42%.

Example 15

Production of 4-(3-pyridyl)-1,2-butanediol

Under argon gas, a solution of diisopropylamine (5.57 g, 55 mmol) in tetrahydrofuran (5 mL) was added dropwise to n-butyllithium (1.53 M in hexane, 31.8 mL, 50 mmol) at 5° C. and the mixture was stirred for 30 minutes. To this was further added a solution of 3-methylpyridine (5.588 g, 30 mmol) in tetrahydrofuran (5 mL) dropwise at 5° C., and the mixture was stirred for 30 minutes. Then, N,N-dimethylaniline (3.64 g, 30 mmol) was added and the mixture was further stirred at 5° C. for 30 minutes. To this was added a solution of glycidol (1.480 g, 20 mmol) in tetrahydrofuran (5 mL) at 5° C., and the reaction was carried out for 2 hours. This reaction mixture was diluted with 30 mL of water for hydrolysis and concentrated under reduced pressure. The residue was extracted with ethyl acetate twice (200 mL each). The organic layers were combined and dried over anhydrous magnesium sulfate. After filtration, the solvent was distilled off under reduced pressure and the residual oil was purified by silica gel column chromatography (Merck's Kieselgel 60, MeOH/ethyl acetate=1/9) to give 2.505 g (isolation yield; 75%) of 4-(3-pyridyl)-1,2-butanediol (yellow oil).

$^1$H-NMR (400 MHz, CDCl$_3$) δ: 1.65–1.88 (m, 2H), 2.63–2.78 (m, 2H), 2.79–2.95 (m, 2H), 3.50 (dd, 1H), 3.62–3.73 (m, 2H), 7.22 (dd, 1H), 7.54 (d, 1H), 8.38–8.50 (m, 2H).

Example 16

Production of 1-O-benzyl-4-(3-pyridyl)-1,2-butanediol

Under argon gas, a solution of diisopropylamine (3.34 g, 33 mmol) in tetrahydrofuran (5 mL) was added dropwise to n-butyllithium (1.53 M in hexane, 19.6 mL, 30 mmol) at 5° C. and the mixture was stirred for 30 minutes. To this was further added a solution of 3-methylpyridine (2.794 g, 30 mmol) in tetrahydrofuran (5 mL) dropwise at 5° C., and the mixture was stirred for 30 minutes. Then, a solution of benzyl glycidyl ether (3.284 g, 20 mmol) in tetrahydrofuran (5 mL) was added at 5° C. and the reaction was carried out for 2 hours. This reaction mixture was diluted with 20 mL of water for hydrolysis, and extracted with 30 mL of ethyl acetate. The organic layer was washed with 20 mL of water twice and the solvent was distilled off under reduced pressure to give 6.248 g of a deep-red oil. This oil was purified by silica gel column chromatography (Merck's Kieselgel 60, hexane/ethyl acetate=1/2) to give 1.50 g (isolation yield: 26%) of 1-O-benzyl-4-(3-pyridyl)-1,2-butanediol (yellow oil).

$^1$H-NMR (400 MHz, CDCl$_3$) δ: 1.63–1.83 (m, 2H), 2.53–2.92 (m, 2H), 3.38 (dd, 1H), 3.49 (d, 1H), 3.80 (m, 1H), 4.57 (s, 2H), 7.21 (m, 1H), 7.25–7.40 (m, 5H), 7.53 (d, 1H), 8.43 (m, 1H), 8.47 (s, 1H).

Example 17

Production of (2R)-4-(3-pyridyl)-1,2-butanediol

Under argon gas, MeOH (70 mL) was added to 10% palladium-on-carbon (1.0 g). Then, the (2R)-1-O-benzyl-4-(3-pyridyl)-1,2-butanediol produced in Example 3 (28.25 g, 100 mmol) and sulfuric acid (19.6 g, 200 mmol) were added. After degassing under reduced pressure, a hydrogen atmosphere was established. The pressure was increased to 3 atm. and the mixture was stirred at room temperature for 16 hours. The palladium-on-carbon was filtered off and the solvent was distilled off under reduced pressure, whereupon a light-yellow oil was obtained. To this oil was added a saturated aqueous solution of sodium hydrogencarbonate for neutralization, followed by concentration under reduced pressure. The residue was extracted with ethyl acetate twice (200 mL each). The organic layers were combined and dried over anhydrous magnesium sulfate. After filtration, the solvent was distilled off under reduced pressure and the oily residue was purified by silica gel column chromatography (Merck's Kieselgel 60, MeOH/ethyl acetate=1/9) to give 10.52 g (isolation yield: 63%) of (2R)-4-(3-pyridyl)-1,2-butanediol (yellow oil).

Under argon gas, a solution of diisopropylamine (5.57 g, 55 mmol) in tetrahydrofuran (5 mL) was added dropwise to n-butyllithium (1.53 M in hexane, 31.8 mL, 50 mmol) at 5° C. and the mixture was stirred for 30 minutes. To this was further added a solution of 3-methylpyridine (5.588 g, 60 mmol) in tetrahydrofuran (5 mL) dropwise ast 5° C., and the mixture was stirred for 30 minutes. Then, N,N-dimethylaniline (3.64 g, 30 mmol) was added and the mixture was further stirred at 5° C. for 30 minutes. To this was added a solution of glycidol (1.480 g, 20 mmol) in tetrahydrofuran (5 mL) at 5° C., and the reaction was carried out for 2 hours. This reaction mixture was diluted with 30 mL of water for hydrolysis and concentrated under reduced pressure. The residue was extracted with ethyl acetate twice (200 mL each). The organic layers were combined and dried over anhydrous magnesium sulfate. After filtration, the solvent was distilled off under reduced pressure and the residual oil was purified by silica gel column chromatography (Merck's Kieselgel 60, MeOH/ethyl acetate=1/9) to give 2.505 g (isolation yield: 75%) of 4-(3-pyridyl)-1,2-butanediol (yellow oil).

$^1$H-NMR (400 MHz, CDCl$_3$) δ: 1.65–1.88 (m, 2H), 2.63–2.78 (m, 2H), 2.79–2.95 (m, 2H), 3.50 (dd, 1H), 3.62–3.73 (m, 2H), 7.22 (dd, 1H), 7.54 (d, 1H), 8.38–8.50 (m, 2H).

What is claimed is:

1. A process for producing a 3-(3-pyridyl)-1-propanol derivative (3):

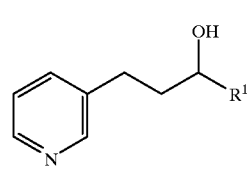

(3)

in the formula, R$^1$ represents an alkyl group of 1 to 20 carbon atoms, aryl group of 6 to 20 carbon atoms or aralkyl group of 7-to-20 carbon atoms, which may be substituted, which comprises reacting a 3-methylpyridine with a strong base to prepare a 3-methylpyridine metal salt (1):

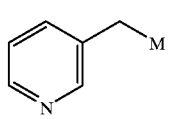

(1)

in the formula, M represents lithium, sodium, potassium or a magnesium halide, where the halide is chloride or bromide, and then reacting said metal salt with an epoxy compound (2):

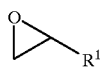
(2)

in the formula, $R^1$ is as defined above,
to give a 3-(3-pyridyl)-1-propanol derivative,
wherein the 3-methylpyridine is used in molar in excess of said strong base.

2. The process according to claim 1 wherein said strong base is a lithium dialkylamide, a lithium disilylamide or a halomagnesium dialkylamide.

3. The process according to claim 2 wherein said strong base is a lithium dialkylamide.

4. The process according to claim 3 wherein said strong base is lithium diisopropylamide.

5. The process according to claim 1, wherein 3-methylpyridine is used in an amount of not less than 1.5 molar equivalents to said strong base.

6. The process according to claim 1, wherein the reaction of said metal salt with said epoxy compound is conducted in the presence of an amine.

7. The process according to claim 6 wherein said amine is a tertiary amine.

8. The process according to claim 7 wherein said tertiary amine is pyridine or triethylamine.

9. The process according to claim 6, wherein said amine is used in not less than an equimolar amount relative to said strong base.

10. The process according to claim 1, wherein the reaction temperature is not less than −20° C.

11. The process according to claim 1, wherein $R^1$ in the epoxy compound (2) is represented by the formula (4):

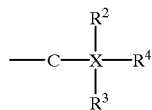
(4)

in the formula, $R^2$ and $R^3$ each independently represents hydrogen, an alkyl group of 1 to 18 carbon atoms, an aryl group of 6 to 18 carbon atoms or an aralkyl group of 7 to 18 carbon atoms, or $R^2$ and $R^3$, taken together, represent a cycloalkyl group of 3 to 18 carbon atoms; $R^4$ represents hydrogen, an alkyl group of 1 to 18 carbon atoms, aryl group of 6 to 18 carbon atoms, aralkyl group of 7 to 18 carbon atoms or silyl group of 3 to 18 carbon atoms, which may be substituted; X represents an oxygen atom or a sulfur atom.

12. The process according to claim 11 wherein $R^2$ and $R^3$ in the formula (4) each represents hydrogen.

13. The process according to claim 11 wherein X in the formula (4) is an oxygen atom.

14. The process according to claim 11, wherein $R^4$ in the formula (4) represents a phenyl group, a benzyl group, a tert-butyl group or a tert-butyldimethylsilyl group.

15. The process according to claim 1, wherein the epoxy compound (2) is optically active.

16. The process according to claim 1, wherein $R^1$ in the formula (2) and (3) represents methyl, ethyl, n-propyl, isopropyl, sec-butyl, tert-butyl, phenyl, benzyl, 2-phenylethyl, 2-(2-naphthyl)ethyl, 2-phenylvinyl, 2-(2-naphthyl)acetylene, chloromethyl, hydroxymethyl, p-toluenesulfonyloxymethyl, acetyloxymethyl, pivaloyloxymethyl, benzoyloxymethyl, phenyloxymethyl, 4-(phenyl)phenyloxymethyl, 4-{3'-(N,N-dimethylphenylacetamido)phenyl}phenyloxymethyl, 2-naphthyloxymethyl, 2-(6-bromonaphthyl)oxymethyl, 2-{6-(3-(N,N-dimethyl)propanamide)naphthyl}oxymethyl, benzyloxymethyl, tert-butyloxymethyl, aryloxymethyl, tert-butyldimethylsilyloxymethyl, 2-tetrahydropyranyloxymethyl, 1-(phenyloxy)ethyl, 1-(phenyloxy)-1-methylethyl, phenylthiomethyl, 2-naphthylthiomethyl, N,N-dimenzylamino, or N-phenyl-N-ethylaminomethyl.

* * * * *